United States Patent [19]

Kamioka et al.

[11] Patent Number: 5,488,311
[45] Date of Patent: Jan. 30, 1996

[54] APPARATUS AND METHOD FOR MEASURING ALCOHOL CONCENTRATION OF LIQUID BLENDED WITH ALCOHOL APPLICABLE TO AN AUTOMOTIVE VEHICLE MOUNTED INTERNAL COMBUSTION ENGINE

[75] Inventors: Hideki Kamioka; Kazumitsu Kobayashi; Masahiko Shimamura, all of Isezaki; Kiyoshi Takeuchi, Yokohama, all of Japan

[73] Assignees: Japan Electronic Control Systems Co., Ltd., Isezaki; Nissan Motor Company, Limited, Yokohama, both of Japan

[21] Appl. No.: 288,427

[22] Filed: Aug. 10, 1994

Related U.S. Application Data

[63] Continuation of Ser. No. 862,646, Apr. 3, 1992, abandoned, which is a continuation-in-part of Ser. No. 705,617, May 29, 1991, abandoned.

[30] Foreign Application Priority Data

May 30, 1990 [JP] Japan .................................. 2-140327

[51] Int. Cl.$^6$ .................................................. G01N 27/22
[52] U.S. Cl. ........................... 324/674; 324/685; 324/686; 73/61.43
[58] Field of Search .................................. 324/674, 667, 324/663, 681, 685, 686; 73/61.43, 61.44

[56] References Cited

U.S. PATENT DOCUMENTS

| | | | |
|---|---|---|---|
| 4,114,090 | 9/1978 | Poskitt | 324/61 |
| 4,470,300 | 9/1984 | Kobayashi | 73/61.43 |
| 4,616,425 | 10/1986 | Burns | 324/667 |
| 4,945,863 | 8/1990 | Schmitz et al. | 73/61.43 |
| 4,971,015 | 11/1990 | Gonze | 73/61.44 |
| 5,005,409 | 4/1991 | Hochstein | 324/674 |
| 5,060,619 | 10/1991 | Sakurai et al. | 123/494 |
| 5,124,655 | 6/1992 | Takeuchi et al. | 324/663 |
| 5,205,151 | 4/1993 | Shimamura et al. | 73/61.43 X |

FOREIGN PATENT DOCUMENTS

| | | | |
|---|---|---|---|
| 3413135 | 10/1985 | Germany . | |
| 3841264 | 11/1989 | Germany . | |
| 0193343 | 11/1984 | Japan | 324/663 |
| 0080843 | 3/1989 | Japan | 324/663 |
| 1-196557 | 8/1989 | Japan . | |

OTHER PUBLICATIONS

Takeuchi et al. "A Capacitance Senor for Methanol Ratio Measurement of Blended Gasoline", IEEE London Meeting, Oct. 28, 1991.

*Primary Examiner*—Kenneth A. Wieder
*Assistant Examiner*—Diep Do
*Attorney, Agent, or Firm*—Foley & Lardner

[57] ABSTRACT

The electrodes of an electrostatic capacitor which is used to determine the alcohol concentration in a mixture of gasoline and alcohol, are connected with a frequency oscillator of the LC type which applies a signal having a frequency which is equal to or greater than 10 MHz. The setting of the oscillation frequency to 10 MHz or more eliminates the amount of change in electrode loss and enables stable and accurate alcohol concentration determination.

11 Claims, 10 Drawing Sheets

FIG. 14a
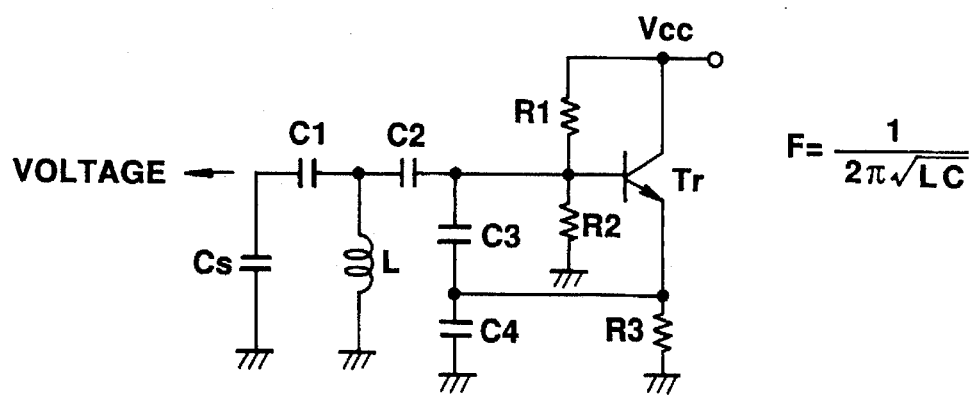
$$F = \frac{1}{2\pi\sqrt{LC}}$$
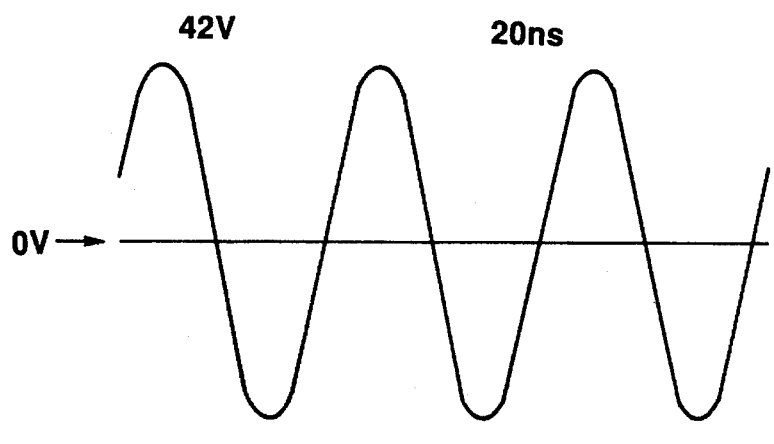
Cs=47pF
F≑15MHz
2V/div.
20ns/div.
LC OSCILLATOR
FIG. 14b

CAPACITANCE, FREQUENCY, AND VOLTAGE
OUTPUT OF THE SENSOR AT 20°C

APPARATUS AND METHOD FOR MEASURING ALCOHOL CONCENTRATION OF LIQUID BLENDED WITH ALCOHOL APPLICABLE TO AN AUTOMOTIVE VEHICLE MOUNTED INTERNAL COMBUSTION ENGINE

This application is a continuation of application Ser. No. 07/862,646, filed Apr. 3, 1992, now abandoned which is a continuation-in-part of application Ser. No. 07/705,617, filed May 29, 1991, now abandoned.

BACKGROUND OF THE INVENTION

1. Field of the Invention

The present invention relates generally to an electrostatic capacitance type alcohol concentration measuring system applicable to a fuel injection system injecting a mixture fuel of gasoline and alcohol (methanol) into an internal combustion engine.

2. Description of the Background Art

When a mixture of gasoline and alcohol (methanol) is used in place of pure gasoline as the fuel of the engine, the stoichiometric air/fuel mixture ratio is naturally changed and it is necessary to change the amount of fuel injected along with the ignition timing and the like.

When gasoline containing 0% of alcohol is supplied to the engine, an injection pulsewidth Ti to be supplied to a corresponding fuel injection valve, the fuel injection pulsewidth corresponding to the fuel injection amount, is determined on the basis of the following equation:

$$Ti = Tp \times \alpha \times \alpha' \times C_{oef} + Ts \quad (1)$$

wherein,

Tp denotes a basic fuel injection quantity;

$\alpha$ denotes a correction coefficient for air/fuel mixture ratio feedback control;

$\alpha'$ denotes a basic air-fuel mixture ratio adaptive correction coefficient;

$C_{oef}$ denotes various correction coefficients; and

Ts denotes a battery voltage variation coefficient.

It is noted that the correction factor (coefficient) $\alpha$ is corrected on the basis of an oxygen concentration signal derived from an oxygen ($O_2$) sensor disposed in an exhaust pipe of the engine and the learning correction coefficient $\alpha'$ is corrected through a learning method on the basis of the basic fuel injection quantity Tp and engine revolution speed N.

Consequently, the stoichiometric air/fuel mixture ratio is controlled to achieve the value of 14.7.

In the way described above, although the stoichiometric air/fuel mixture ratio for pure gasoline is 14.7, the air/fuel mixture ratio A/F is controlled to provide a value of 6.5 in a case of the fuel having the ratio of 100% alcohol concentration of methanol. Therefore, it is necessary to change the stoichiometric air/fuel mixture ratio by about twice in the range of the alcohol concentration of 0 through 100%.

Hence, in a case where the alcohol blended gasoline is used as the fuel, it is necessary to calculate the fuel injection quantity Ti' from the equation (1) as follows:

$$Ti' = M_k \times Tp \times \alpha \times \alpha' \times C_{oef} + Ts \quad (2)$$

wherein, $M_k$ denotes a constant determined according to the alcohol concentration.

Therefore, in a case where the alcohol blended gasoline is used for the fuel supplied to the engine, a measuring instrument such as an alcohol sensor is installed to generate an output voltage corresponding to the alcohol concentration and to calculate the equation of (2) on the basis of the generated output voltage value.

The measuring instrument described above includes a resistance type alcohol concentration measuring system which detects the concentration of alcohol from electric conductivities of the gasoline and alcohol; an electrostatic capacitance type alcohol concentration measuring apparatus utilizing a change in a dielectric constant (permitivity) of the alcohol blended gasoline; and an optical type alcohol concentration measuring apparatus utilizing a light index of refraction.

FIGS. 7 through 13 show a fuel injection control system disclosed in U.S. Pat. Nos. 5,205,151 and 5,060,619 which incorporates the alcohol sensor of the type which utilizes the change in the electrostatic capacitance described above.

The arrangement of the whole engine shown in FIG. 7 includes an internal combustion engine 1, a fuel injector 2, an induction manifold 3, an air cleaner 4, an air flow meter 5, an exhaust manifold 6 which includes an $O_2$ sensor (not shown), a fuel tank 7 containing an alcohol blended gasoline 8, a fuel pump 9, a fuel supply conduit 10, a filter 11 which is disposed in the supply conduit 10, a pressure regulator 12 and a return conduit via which fuel is returned to the fuel tank 7.

The arrangement further includes an alcohol concentration sensor 14 which is disposed in the fuel supply conduit at a location downstream of the filter 11 and which is arranged to output a signal indicative of the amount of alcohol contained in the fuel being pumped through the supply conduit 10.

This alcohol concentration sensor 14 is constituted by a pair of electrode plates in a form of a pair of flat parallel metallic plates or of a coaxial cylindrical tube installed in the fuel conduit 10.

In the case of the pair of flat parallel plates described above, an electrostatic capacitance Cs is expressed as follows:

$$Cs = \epsilon S/d \quad (3)$$

wherein $\epsilon$ denotes an permitivity, S denotes an electrode area, and d denotes a distance in space between electrodes.

An electrostatic capacitance defined as above is detected by an electrostatic capacitance detector 15.

An oscillation frequency f of an LC oscillator 16 is expressed by the following equation (4):

$$f = 1/2\pi\sqrt{L(Cs + Co)} \quad (4)$$

wherein L denotes an inductance; and

Co denotes a capacitance that the circuit inherently has.

In addition, a frequency/voltage (F/V) converter 17 to convert the oscillation frequency f into the detection voltage V is provided. Furthermore, an inverting amplifier 18 inverts and amplifies the detected voltage V from the F/V converter 17 and outputs an output voltage Vo.

In more detail, the alcohol blended gasoline 8 has the relationship of the alcohol concentration M to the permitivity $\epsilon$ shown by the characteristic of FIG. 9.

FIG. 10 shows a relationship between the electrostatic capacitance Cs detected by the electrostatic capacitance detector 15 and alcohol concentration M.

The detected voltage V produced by means of the F/V converter 17 is represented by the characteristic shown in FIG. 11.

This is inverted and amplified with the inverting amplifier 18. Consequently, the output voltage Vo has the characteristic shown in FIG. 12.

Thus, the alcohol concentration measuring apparatus 14 can provide the output voltage Vo having the characteristic shown in FIG. 12 with respect to the alcohol concentration M.

Numeral 19 denotes a temperature responsive sensor comprising a thermistor or posister detecting a fuel temperature (hereinafter, referred to as a fuel temperature) of the alcohol blended gasoline 8, installed mid-way in the fuel conduit 10. The detected temperature t by means of the temperature sensor 19 is input into an alcohol concentration temperature correcting apparatus 21 as will be described later (and a fuel injection pulsewidth calculation circuit 22), the alcohol concentration M being corrected in terms of the temperature.

In addition to the above-described data inputs, the control unit receives a plurality of other data such as an input data on engine crank angle sensor 23, an engine coolant temperature and so on.

As shown in FIG. 9, the capacitance type alcohol concentration sensor 14 is such that as the alcohol concentration M increases, its permitivity $\epsilon$ (dielectric constant) accordingly increases. Therefore, the change in the permitivity causes the change in the electrostatic capacitance Cs, the change in the capacitance being detected and being monitored from the output voltage change.

It is noted that the permitivity $\epsilon$ varies not with the change in the alcohol concentration but only also with the change in temperature. Consequently, the output voltage Vo from the electrostatic capacitance type alcohol concentration measuring apparatus 14 has a temperature dependent characteristic with respect to a fuel temperature t as shown in FIG. 13.

That is to say, the output voltage Vo of the alcohol concentration measuring apparatus M generated is such that the output voltage increases as the fuel temperature decreases with respect to the same alcohol concentration M.

Therefore, the control unit 20 performs the function of the alcohol concentration temperature correction apparatus 21 by software. An input of the alcohol concentration temperature correction apparatus 21 is connected to the alcohol concentration measuring apparatus 14 and the temperature responsive sensor 19 and an output thereof is connected to the fuel injection quantity calculating apparatus 22. The alcohol concentration temperature correcting apparatus 21 corrects the output voltage Vo from the inverting amplifier 18 in terms of the temperature on the basis of the detected temperature t from the temperature responsive sensor 19. The alcohol concentration temperature correcting apparatus 21 internally includes storage elements such as RAM and ROM in which is stored a temperature correction map 21A. The map 21A represent a relationship between the alcohol concentration M and output voltage Vo for each detected temperature t, so that, for example, a standard output voltage after correction corresponding to 20° C. and a standard alcohol concentration after correction is output.

Furthermore, the fuel injection calculation apparatus 22 in the control unit 20 has an input connected to the alcohol concentration temperature correction apparatus 21, crank angle sensor 23, air-flow meter 5, an oxygen sensor and a coolant temperature sensor (not shown) and an output connected to a fuel injection valve 2 through which the engine fuel is injected.

The fuel injection quantity calculation apparatus 22 described above calculates the basic fuel injection quantity Tp on the basis of the engine revolution speed N from the crank angle sensor 23 and the intake air quantity Q from the air-flow meter 5, calculates the fuel injection quantity Ti' according to the equation (2) on the basis of the standard output voltage after correction or standard alcohol concentration after correction from the alcohol concentration temperature correction apparatus 21 and other signals from the various sensors, and outputs a fuel injection pulse having a duty ratio corresponding to the calculated fuel injection quantity Ti' to the fuel injection valve 2.

When the alcohol concentration measuring apparatus 14 is applied to the fuel injection controlling apparatus, the structure thereof is as described above. The electrostatic capacitance detector 15 detects the electrostatic capacitance Cs from the equation (3) corresponding to the alcohol concentration M. The oscillation circuit 16 oscillates at the frequency f according to the equation (4) corresponding to the alcohol concentration M, outputs the detected voltage V corresponding to the the frequency f by means of the f-V converter 17, and outputs the output voltage Vo after inverted amplification in the inverting amplifier 18.

On the other hand, the control unit 20 includes the alcohol concentration temperature correction apparatus 21 which serves to carry out the temperature correction of the alcohol concentration on the basis of the output voltage Vo from the alcohol concentration measuring apparatus 14 and outputs to the fuel injection quantity calculating apparatus 22 the standard output voltage or standard alcohol concentration corresponding to, e.g., 20° C.

Thus, the calculation of the fuel injection quantity Ti' according to the equation (2) on the basis of the standard alcohol concentration without influence of the temperature can be executed so that highly accurate injection of fuel can be achieved.

However, in the previously proposed alcohol concentration measuring apparatus described above, since a low oscillation frequency (100 KHz or less) is used as the oscillation frequency f of the LC type oscillator 16, its oscillation frequency has variations in frequency due to the influence of conductive materials (metallic ions etc.,.) impregnated in the fuel so that the detected voltage becomes unstable. Therefore, the calculation of the fuel injection quantity Ti' by the fuel injection quantity calculating apparatus 22 becomes inaccurate and accurate control of the air/fuel mixture ratio cannot be achieved.

SUMMARY OF THE INVENTION

It is therefore an object of the present invention to provide an apparatus for stably and accurately measuring an alcohol concentration of an electrostatic capacitance utilizing a predetermined range of an oscillation frequency of an oscillator which is relatively higher than the previously proposed apparatus.

The above-described objects can be achieved by providing an apparatus for measuring an alcohol concentration of a liquid blended with alcohol, comprising: a) an electrostatic capacitance detector, having its electrodes immersed in the liquid, for detecting the alcohol concentration in terms of an electrostatic capacitance between its electrodes; b) an oscillator which oscillates at a frequency based on the electrostatic capacitance detected by the electrostatic capacitance detector; and, c) a frequency-to-voltage converter which converts the frequency output by the oscillator to the corresponding voltage, and wherein said oscillator oscillates at a frequency in a range of frequency of 10 MHz or more when the concentration of alcohol ranges from 0% to 100%.

The above-described object can also be achieved by providing in a fuel injection quantity control system for an internal combustion engine which is adapted to be operated upon a mixture of gasoline and alcohol, sensor means for determining engine speed and load; an alcohol concentration sensor for sensing the amount of alcohol which is contained in the fuel to be injected, the alcohol concentration sensor having: electrodes which are immersed in the fuel in a manner to integrally define a capacitor; an oscillator which is operatively coupled to the electrodes and arranged to apply a signal having a frequency of 10 MHz or more, thereto; and circuit means responsive to the alcohol concentration sensor and the sensor means for determining an injection pulsewidth.

BRIEF DESCRIPTION OF THE DRAWINGS

FIG. 8 is a circuit block diagram of a previously proposed alcohol concentration measuring apparatus.

FIG. 9 is a diagram representing a relationship between the alcohol concentration and dielectric constant.

FIG. 10 is a diagram representing a relationship between the alcohol concentration and permitivity detected.

FIG. 11 is a diagram representing the alcohol concentration and permitivity.

FIG. 12 is a diagram representing the alcohol concentration and detected voltage derived from the F/V converter.

FIG. 13 is a diagram representing the alcohol concentration for each fuel temperature and output voltage derived from the inverting amplifier.

FIG. 14 is a circuit wiring diagram of an oscillator used in the preferred embodiment shown in FIG. 5 according to the present invention.

DETAILED DESCRIPTION OF THE PREFERRED EMBODIMENTS

Reference will hereinafter be made to the drawings in order to facilitate a better understanding of the present invention.

Figure 1:
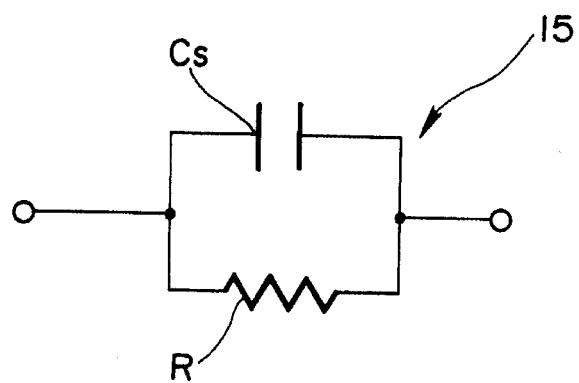
FIG. 1 is a circuit wiring diagram of a first preferred embodiment in which an equivalent circuit of an electrostatic capacitance detector is shown.

During experiments conducted in connection with the above-mentioned oscillation frequency scattering it was determined that the shape of the capacitor electrodes was not a problem and that, as shown in the circuit diagram in FIG. 1, the internal resistance R and the capacitance Cs could be considered as being in a parallel circuit.

As a result, the relationship which existed between the electrode loss D which results from the internal resistance R and capacitance Cs of the capacitor 15, and the oscillation frequency f produced by the oscillator was investigated. As a result it was observed that the largest changes in the electrode loss D and oscillation frequency scattering occurred in low frequency ranges.

Figure 2:
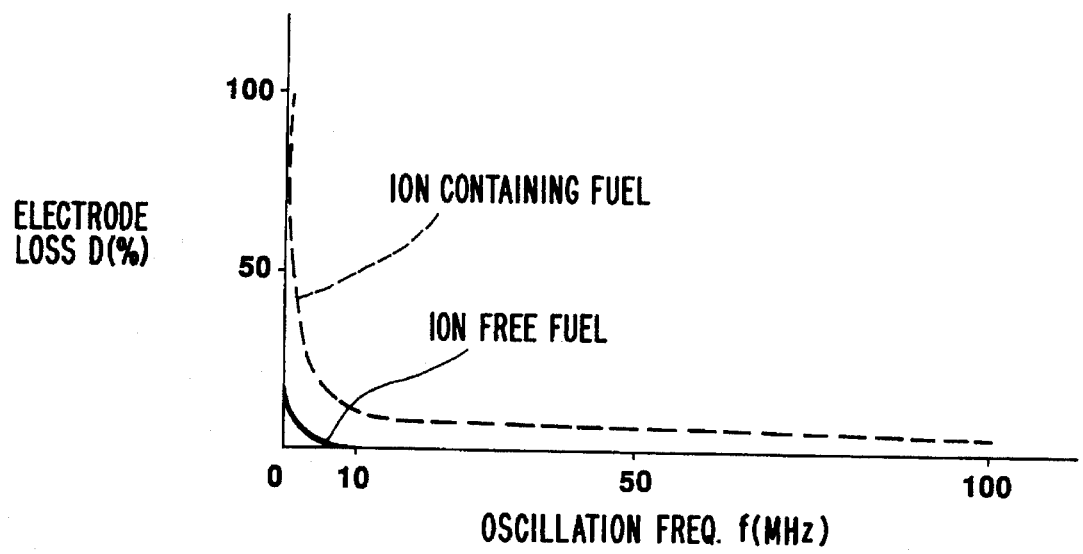
FIGS. 2 is a diagram of a relationship between an oscillation frequency during 85% of the alcohol concentration and electrode loss.
Figure 3:
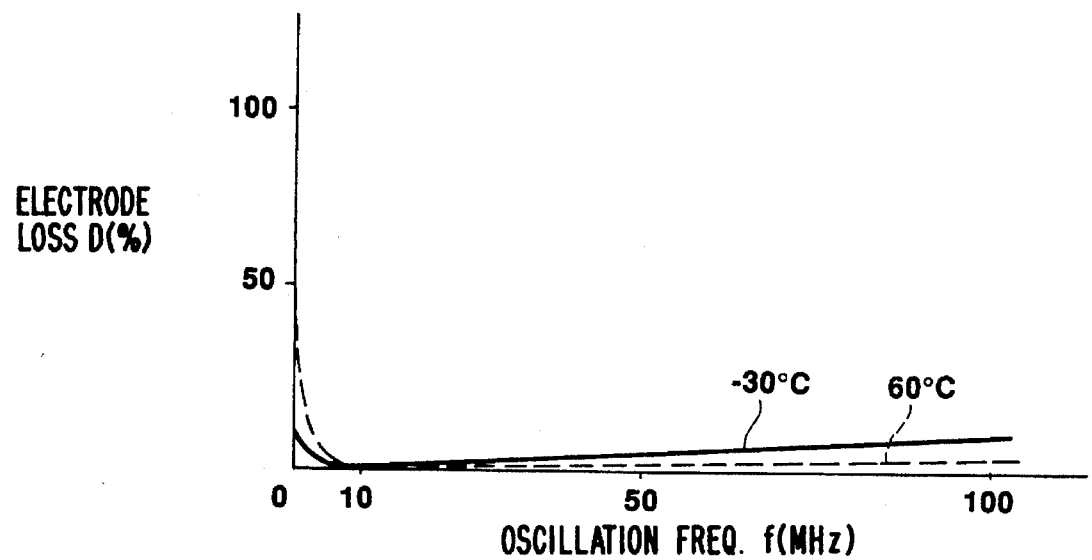
FIG. 3 is a diagram of a relationship between the oscillation frequency and electrode loss during −30° C. and 60° C. of temperature in a case where the metallic ions are not included.

FIGS. 2 and 3 show results obtained from these so experiments.

It will be noted that the electrode loss D of the capacitor 15 is given by the following equation:

$$D = 1R/2\pi fCs \qquad (5)$$

wherein R denotes the internal resistance of the capacitor electrodes.

In FIG. 2, the solid line trace A denotes the electrode loss D—oscillation frequency f characteristics which are obtained with fuel which contains 85% alcohol (hereinafter indicated by M85) at the fuel temperature of 20° C. which contains no metallic ions, while the broken line trace denotes the characteristics obtained with M85 at 20° C. which did contain the metallic ions.

As is clear from FIG. 2, when the frequency f falls in a range of less than 10 MHz zone the electrode losses D exhibit mutual acute changes in characteristics. Especially, in the range of frequency which the previously proposed oscillator used as the oscillation frequency, the change in the electrode loss D was rapid in the case of the inclusion of the metallic ions and was not so rapid in the case of no inclusion of the metallic ions.

On the other hand, in each characteristic graph, a minute change in the frequency region less than 100 KHz caused a rapid change in the electrode loss D.

Therefore, the variation in the oscillation frequency f occurs according to the frequency range of the set oscillation frequency f and the detected voltage became unstable.

FIG. 3 indicates the same result of the experiment as in FIG. 2 in a case where the fuel temperature is different.

The solid line of FIG. 3 indicates the characteristic line at −30° C. for the fuel temperature and the broken line of FIG. 3 indicates the characteristic line at 60° C. for the fuel temperature.

As is appreciated from FIG. 3, the rapid change in the electrode D was observed in the range less than 10 MHz of the frequency f in either case the of characteristic line.

Hence, for use of a frequency less than 100 KHz, the variation in the oscillation frequency f occurred. Furthermore, in a range higher than the oscillation frequency f, the change in the electrode loss D occurred although its gradient was moderate.

Figure 4:
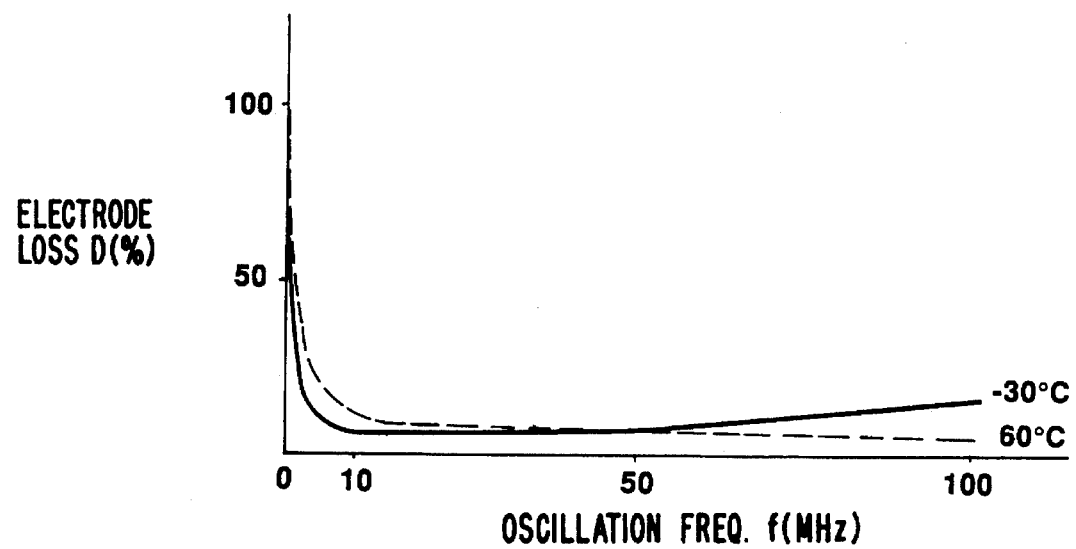
FIG. 4 is a diagram representing the relationship of the same oscillation frequency as FIG. 3 and electrode loss.

Furthermore, FIG. 4 shows the same result of the experiment as in FIG. 3 in the case in which the inclusion of the metallic ions is shown.

As is appreciated from FIG. 4, in a case where the metallic ions are included, it was indicated that the electrode loss D was largely influenced according to the fuel temperature in the frequency range less than 10 MHz.

With the result of the series of the experiments taken into account, the variation in the oscillation frequency f can be prevented if the oscillation frequency f in the high frequency range (10 MHz or more) is used. In addition, the accurate detection of the alcohol concentration can be obtained.

It is further noted that the electrode loss D becomes more stable if the oscillation frequency f is located in the vicinity to 50 MHz, e.g., 40 through 60 MHz and the highly accurate output voltage can be obtained. That is to say, when the fuel temperature is low, a resonance frequency of molecules in the methanol is lowered. Therefore, the electrode loss D accompanying the resonance (variance) is slightly increased so that the electrode loss D in the higher frequency side provides accordingly a slightly larger value. However, as shown in FIG. 4, the electrode loss D in the vicinity to 50 MHz becomes especially stable.

Figure 5:
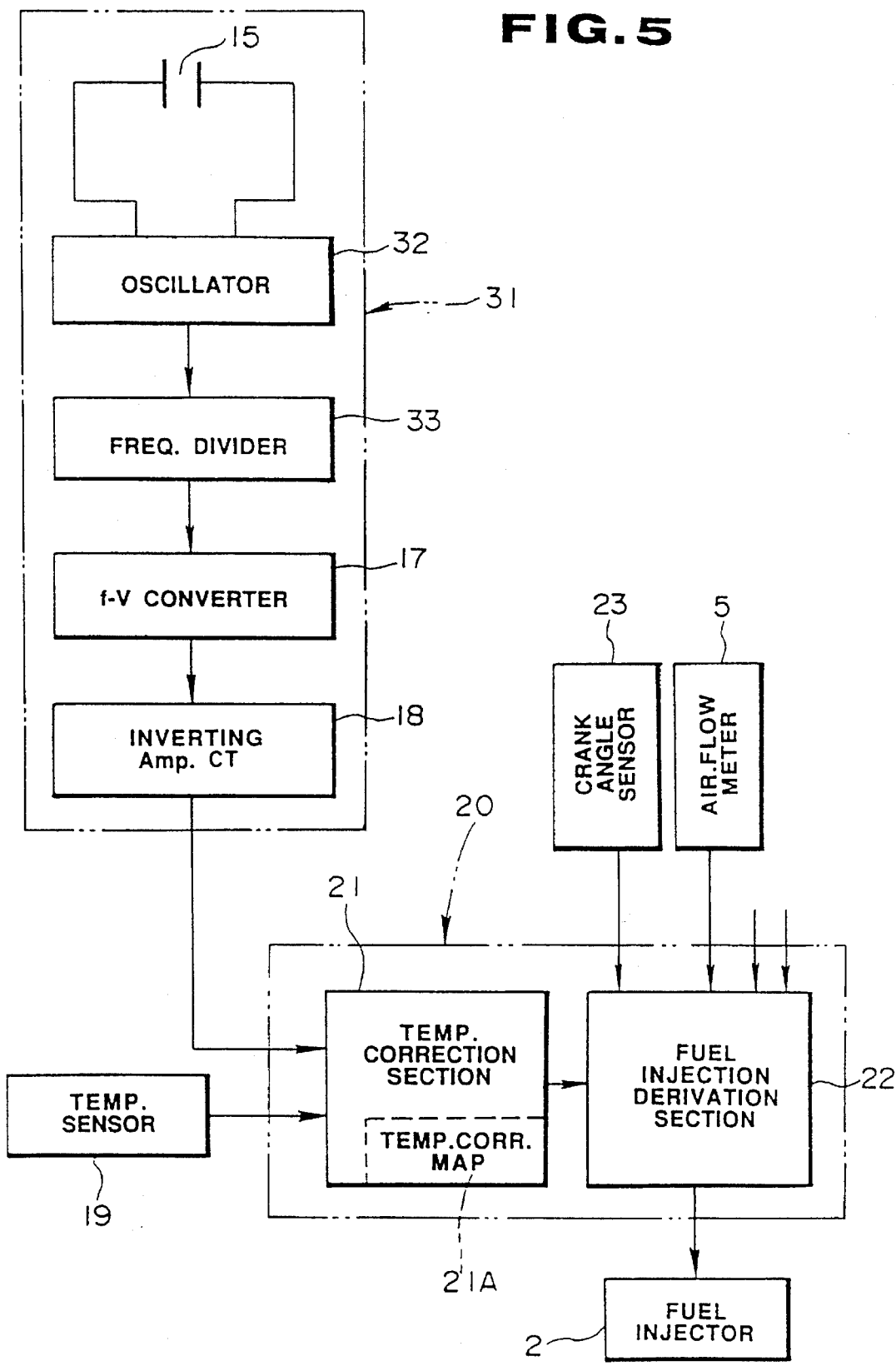
FIG. 5 is a circuit block diagram of an electrostatic capacitance type alcohol concentration measuring apparatus.

FIG. 5 shows a specific example of the alcohol concentration measuring apparatus in the preferred embodiment. The explanations of the same reference numerals in FIG. 5 as those in the previously proposed alcohol measuring apparatus are omitted here.

In FIG. 5, numeral 31 denotes the electrostatic capacitance type alcohol concentration measuring apparatus.

The alcohol concentration measuring apparatus 31 has a structure substantially the same as in the previously proposed alcohol concentration measuring apparatus 14, i.e., as disclosed in Japanese Patent Application First Publication No. Heisei 1-196557, including the electrostatic capacitance detector 15 installed midway through the fuel conduit 10 for detecting the alcohol concentration in the alcohol blended gasoline 8.

In FIG. 5, numeral 32 denotes the oscillator in the preferred embodiment which oscillates at the oscillation frequency f shown in the equation (4) together with the electrostatic capacitance of Cs in the electrostatic capacitance detector 15. Especially, when the alcohol concentration is varied in the range from 0% to 100%, the oscillator can oscillate at the oscillation frequency f of 10 MHz or more. Numeral 33 denotes the frequency divider interposed between the oscillator 32 and F/V converter 17 for eliminating noise such as ringing generated in the sensor circuitry.

The operation of the alcohol concentration measuring apparatus in the preferred embodiment is substantially the same as in the previously proposed apparatus.

A structure of the oscillator 32 is exemplified in FIG. 14a.

In order to provide oscillation signal having the oscillation frequency of 10 MHz or more for the oscillator 32, the values of L and Co need to be set which satisfy the following equation (5) (Co denotes a resultant capacitance in the series circuit of $C_1$, $C_2$, $C_3$, and $C_4$ in the circuit shown in FIG. 14):

$$10 \text{ MHz} \leq f_{MIN} = 1/2\pi \sqrt{L(Cs_{MAX} + Co)} \quad (5)$$

wherein $Cs_{MAX}$ denotes a maximum value of Cs, i.e., the value of Cs when the alcohol concentration indicates 100% and $f_{MIN}$ is a minimum value of the ocsillation frequency f, i.e., a value of frequency f when $Cs_{MAX}$.

Figure 15:
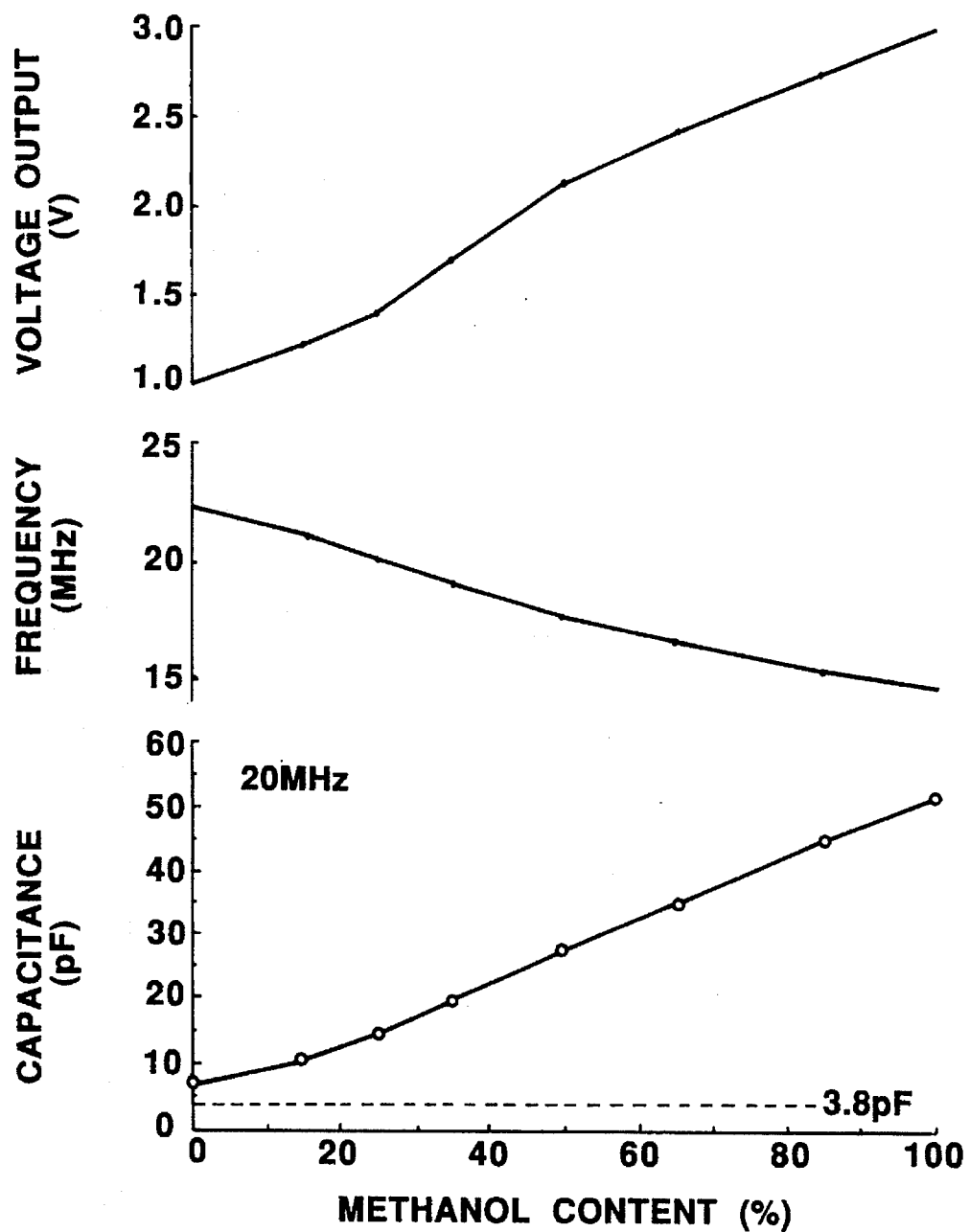
FIG. 15 is charateristic graphs of electrostatic capacitance, frequency, and voltage output of the alcohol concentration sensor at 20° C. with respect to the concentration of alcohol.

FIG. 15 shows characteristic graphs of capacitance (pf), frequency (MHz), and voltage output (V) with respect to the alcohol content (%) at 20° C. when using the LC oscillator shown in FIG. 14a.

It is noted that FIGS. 14a and b and 15 are described in the English paper titled A CAPACITANCE SENSOR FOR METHANOL RATIO MEASUREMENT OF BLENDED GASOLINE authored by H. Kamioka, M. Shimamura, and K. Kobayashi announced at a London Meeting of the IEEE, Oct. 28, 1991.

Since, in the alcohol concentration measuring apparatus 31 in the preferred embodiment, the oscillation frequency f of the oscillator 32 is set to the range of 10 MHz or more, the influence of the electrode loss D is less and variation in the oscillation frequency can effectively be prevented. Furthermore, since the divider 33 is used to divide the oscillation frequency, the effect of noise such as ringing generated in the sensor circuitry can be reduced and accurate detection of alcohol concentration can be achieved.

In the fuel injection quantity calculation apparatus 22, the calculation of the fuel injection quantity Ti' according to the equation (2) is carried out. Therefore, the appropriate air/fuel mixture ratio can be controlled and accurate fuel injection control can be achieved.

Figure 6:
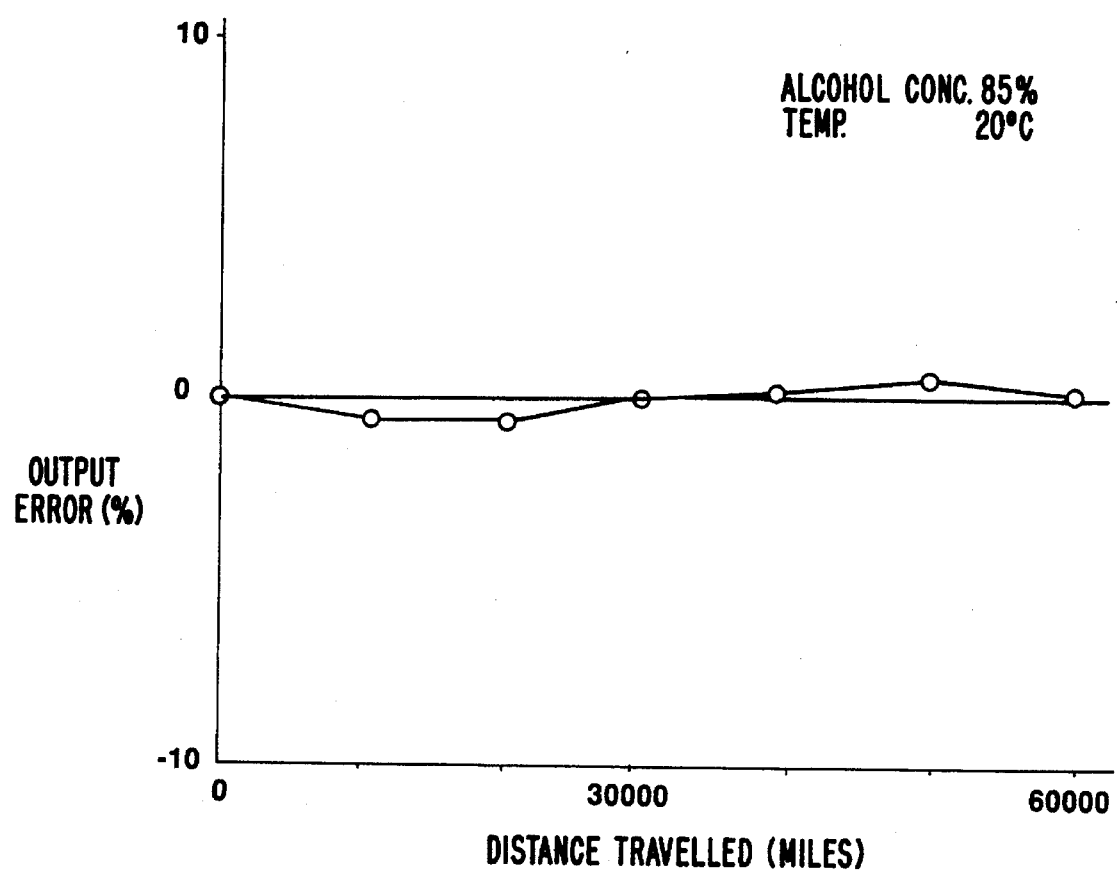
FIG. 6 is a circuit wiring diagram indicating a result of endurance test in the alcohol concentration measuring apparatus.
Figure 7:
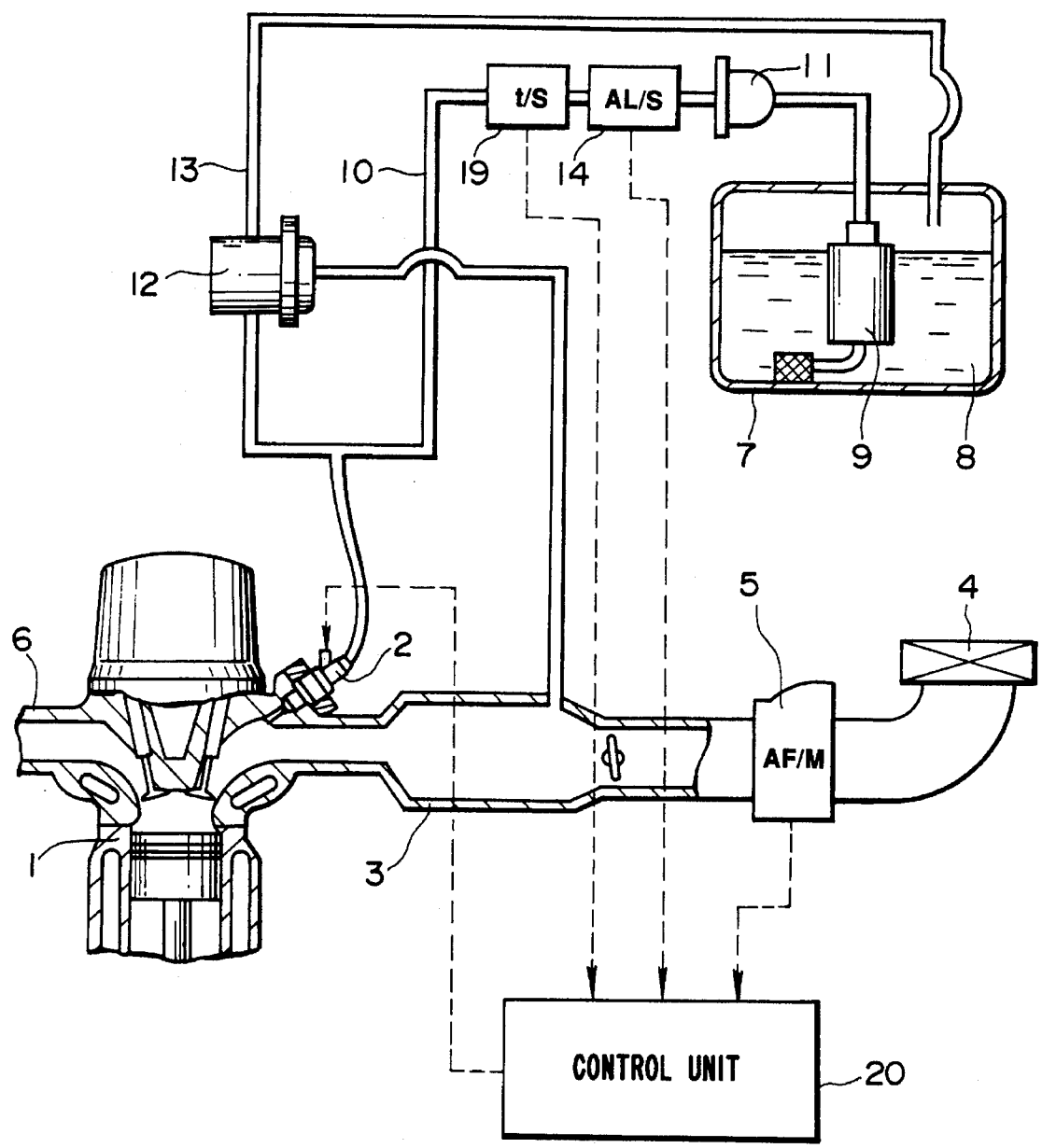
FIGS. 7 through 13 show previously proposed electrostatic capacitance type alcohol concentration measuring apparatus.
Figure 8:
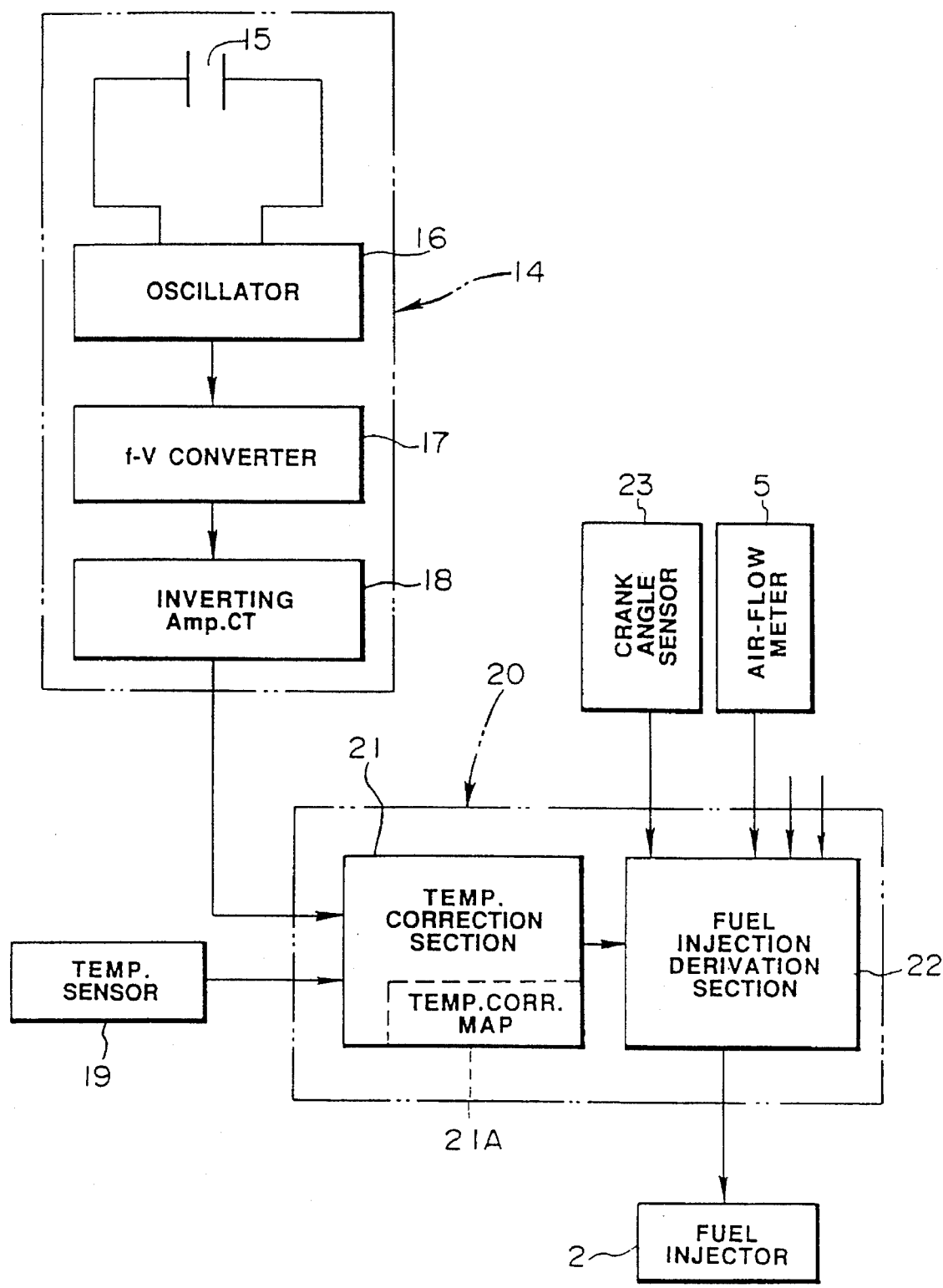
Figure 9:
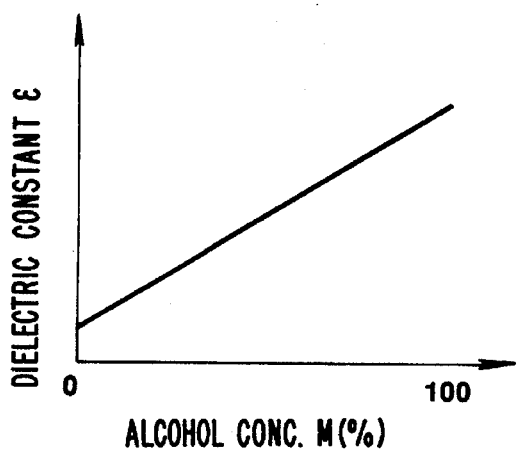
Figure 10:
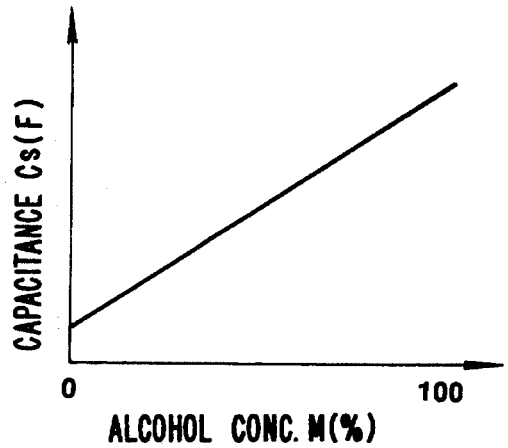
Figure 11:
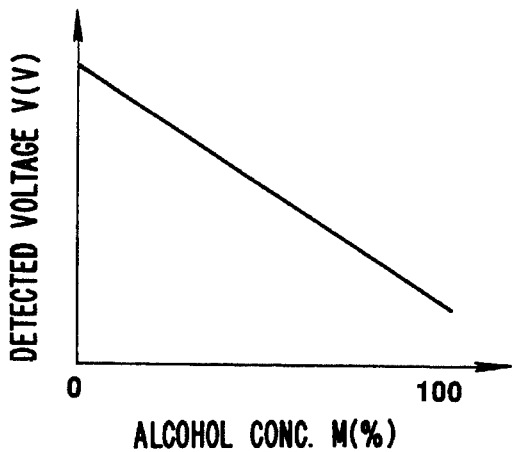
Figure 12:
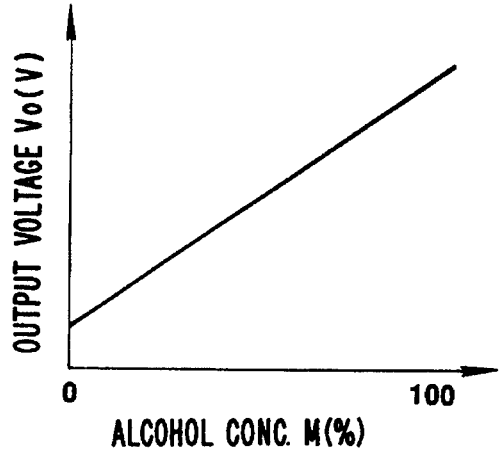
Figure 13:
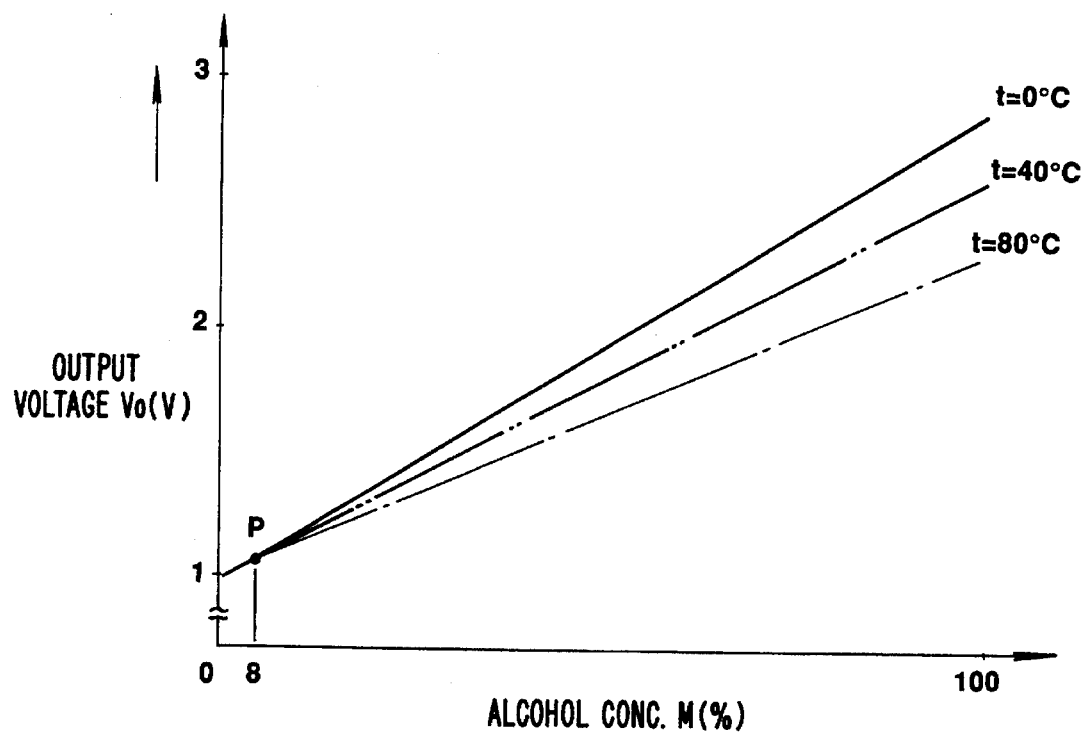

As the result of endurance experiments when the alcohol concentration measuring apparatus 31 was actually mounted in a vehicle, hardly any output error was found and a stable output voltage was observed during the long run of the vehicle (long distance run), as is appreciated from FIG. 6.

Although in the preferred embodiment the alcohol concentration temperature correction apparatus 21 is used to correct the alcohol concentration in terms of temperature, it is possible to omit the temperature correction if the range of the oscillation frequency f is appropriately selected.

Furthermore, if the oscillation frequency f of the oscillator 32 is set in the range from 13 MHz to 21 MHz which corresponds to the alcohol concentration range from 0 to 100% to measure the alcohol concentration in the fuel, the extremely accurate fuel injection quantity Ti' can be controlled.

As described hereinabove, since according to the present invention the pair of electrodes are immersed in the liquid blended in the alcohol, the electrostatic capacitance detector which detects the electrostatic capacitance between the electrodes is installed, the detector is connected to the oscillator whose oscillation frequency is varied according to the electrostatic capacitance, the oscillation frequency is converted into the voltage to detect the alcohol concentration, and the oscillation frequency is set to the range over 10 MHz or more in the range of the alcohol concentration from 0% to 100%, the variation of the oscillation frequency f due to the metallic ions dissolved in the liquid can be eliminated and erroneous detection of the alcohol concentration of the alcohol concentration measuring apparatus can be prevented. The accurate detection of the alcohol concentration can be achieved. In addition, if the fuel injection quantity control uses the alcohol concentration measuring apparatus, the appropriate air/fuel mixture ratio control can be achieved and highly accurate fuel injection control can be achieved. Furthermore, if the oscillation frequency range is appropriately selected, the temperature correction processing can be omitted. Various other effects can be exhibited according to the present invention.

A U.S. Pat. No. 4,114,090 issued on Sep. 12, 1978 discloses a moisture detection unit for sensing the moisture content of tobacco. In the disclosed moisture content detection unit, the capacitor sensor forming part of the C. R. network is arranged. The oscillation frequency of the oscillator in the above-identified U.S. Patent is 0 to 10 KHz in the same way as described in the BACKGROUND OF THE INVENTION.

However, in the present invention, the oscillation frequency of the oscillator 32 is 10 MHz or more as defined by the appended claims.

A minimum limit of the oscillation frequency is an essential subject matter of the present invention. The effects of providing the minimum oscillation frequency are already described above.

A U.S. Pat. No. 4,939,468 issued on Jul. 3, 1990 discloses the capacitive fluid sensor for sensing the dielectric constant of fluid, the sensor including the sensor housing, the fluid outlet pipe connected midway through the sensor housing, the internal electrode, the first cylindrical insulating internal electrode support member disposed within the sensor housing between the fluid outlet pipe and the sensor housing end and the sealing member disposed within the sensor housing between the first cylindrical support member and sensor housing end. FIG. 22 of the above-identified U.S. Patent shows the arrangement of the circuit section of the fluid sensor. However, no oscillation frequency of the oscillator is disclosed and structure of the oscillator is quite different from that according to the present invention.

It will fully be appreciated by those skilled in the art that the foregoing description has been made with regard to the preferred embodiments and various changes and modifications may be made without departing from the scope of the present invention which is to be defined by the appended claims.

What is claimed is:

1. An apparatus for measuring an alcohol concentration of a liquid blended with alcohol, comprising:
   a) an electrostatic capacitance detector, having electrodes immersed in said liquid, for detecting an electrostatic capacitance between said electrodes;
   b) an oscillator coupled to said electrostatic capacitance detector and configured to oscillate at a frequency based on an amount of said electrostatic capacitance detected by said electrostatic capacitance detector, said oscillator oscillates at said frequency in a frequency range of 10 Mhz or more dependent on said alcohol concentration;
   c) a frequency divider coupled to said oscillator and configured to divide said frequency from said oscillator and to output a divided frequency indicative thereof; and
   d) a frequency-to-voltage converter coupled to said frequency divider and configured to convert said divided frequency into a corresponding voltage.

2. A method for measuring an alcohol concentration of a liquid blended with alcohol, comprising the steps of:
   a) forming an oscillation circuit coupled to an electrostatic capacitance sensor having mutually opposing electrodes, said electrodes being immersed in the liquid such that a dielectric constant of said electrostatic sensor is varied with the alcohol concentration of the liquid, wherein an electrostatic capacitance of said electrostatic capacitance sensor is varied with the alcohol concentration, said oscillation circuit outputting an output frequency as an oscillation frequency based on said electrostatic capacitance;
   b) dividing the output frequency by a frequency divider and outputting a divided frequency, said divided frequency being at a lower frequency than the output frequency;
   c) converting said divided frequency into a first voltage, a level of said first voltage corresponding to the alcohol concentration;
   d) detecting a temperature of the liquid; and
   e) compensating the level of said first voltage for a variation in the detected temperature to derive a second voltage which indicates the alcohol concentration and which is compensated according to the variation in the temperature of the liquid,
   wherein said oscillation frequency of said oscillation circuit is selected to be in a frequency range of greater than 10 MHz but less than 60 MHz when the alcohol concentration ranges from 0% to 100%, such that an electrode loss caused by resonance of said electrodes is reduced and the electrode loss affecting the indicated value of the second voltage is stable.

3. A method for measuring alcohol concentration of a liquid blended with alcohol as recited in claim 2, wherein the frequency range of the oscillation frequency is between 40 MHz and 60 MHz.

4. A method for measuring alcohol concentration of a liquid blended with alcohol as recited in claim 2, wherein the liquid comprises gasoline for an internal combustion engine and the alcohol is methanol.

5. A fuel injection quantity control system for an internal combustion engine which is injected with fuel which includes a mixture of gasoline and alcohol, said fuel being injected to said internal combustion engine by a plurality of fuel injectors, said system comprising:
   sensor means for determining speed and load of said internal combustion engine;
   an alcohol concentration sensor for sensing an amount of alcohol contained in said fuel having a concentration of said alcohol ranging from 0% to 100%, said alcohol concentration sensor having electrodes which are immersed in said fuel to integrally define a capacitor;
   an oscillator operatively coupled to said electrodes together with the alcohol concentration sensor and configured to provide a oscillation signal having a frequency of more than 10 MHz;
   a frequency divider coupled to said oscillator and configured to divide the frequency of said oscillation signal and to output a divided frequency signal as a result thereof, said divided frequency signal having a frequency less than the frequency of the oscillation signal; and
   circuit means responsive to said divided frequency signal provided from said frequency divider for determining an appropriate pulsewidth of a fuel injection signal to be applied to said plurality of fuel injectors,
   wherein said oscillation signal produced by said oscillator varies according to the concentration of said alcohol,
   and wherein the pulsewidth of said fuel injection signal determines an amount of said fuel to be injected into said internal combustion engine by said fuel injectors.

6. A fuel injection quality control system as recited in claim 5, wherein, when said signal having a frequency higher than 10 MHz is produced by said oscillator coupled to said electrodes, an electrode loss due to resonance of said electrodes is reduced.

7. A fuel injection quality control system as recited in claim 6, wherein said signal produced by said oscillator has a frequency in a range from 40 MHz to 60 MHz.

8. A fuel injection quality control system as recited in claim 5, wherein said oscillator comprises an LC circuit having a capacitance including said electrodes.

9. A fuel injection quality control system as recited in claim 8, further comprising:
   a temperature sensor immersed in said fuel for detecting a temperature of said fuel and outputting a temperature detection signal therefrom; and
   temperature correcting means connected to said frequency-to-voltage converter and said temperature sensor for correcting said voltage signal indicative of a value of alcohol concentration output from said frequency-to-voltage converter according to said temperature detection signal output from said temperature sensor.

10. A method for measuring an alcohol concentration of a liquid blended with alcohol, comprising the steps of:

a) measuring an electrostatic capacitance of said liquid;

b) determining an oscillation frequency according to said electrostatic capacitance, said oscillation frequency varying according to a level of said electrostatic capacitance;

c) dividing said oscillation frequency into a divided frequency;

d) converting said divided frequency into a first voltage, said first voltage indicating the alcohol concentration of the liquid;

e) detecting a temperature of the liquid; and f) adjusting said first voltage based on the detected temperature to derive a second voltage which indicates the alcohol concentration and which is compensated according to the variation in the temperature of the liquid, wherein said oscillation frequency is selected to be in a frequency range of greater than 10 MHz but less than 60 MHz when the alcohol concentration ranges from 0% to 100%, such that an electrode loss caused by resonance of said electrodes is reduced and the electrode loss affecting a value of said second voltage is stable.

11. A fuel injection quantity control system for an internal combustion engine which is injected with fuel which includes a mixture of gasoline and alcohol, said fuel being injected to said internal combustion engine by a plurality of fuel injectors, said system comprising:

a sensor circuit connected to said internal combustion engine and configured to determine a speed and load of said internal combustion engine and to output a sensor signal indicative thereof;

an alcohol concentration sensor configured to sense an amount of alcohol contained in said fuel having a concentration of said alcohol ranging from 0% to 100%, said alcohol concentration sensor having electrodes which are immersed in said fuel to integrally define a capacitor;

an oscillator operatively coupled to said alcohol concentration sensor and configured to produce a fixed frequency signal having a frequency of more than 10 MHz, said frequency of said fixed frequency signal being proportional to the amount of alcohol sensed by said alcohol concentration sensor;

a frequency divider coupled to said oscillator and configured to divide said frequency of said fixed frequency signal and to output a divided frequency signal as a result thereof: and a signal generation circuit means coupled to receive said divided frequency signal from said frequency divider and said sensor signal from said sensor circuit and configured to determine a pulsewidth of a fuel injection signal to be applied to said plurality of fuel injectors, wherein said fixed frequency signal produced by said oscillator varies according to the concentration of said alcohol, and the pulsewidth of said fuel injection signal determines an amount of said fuel to be injected into said internal combustion engine by said fuel injectors, and wherein when said fixed frequency signal is output from said oscillator, an electrode loss due to resonance of said electrodes is reduced.

* * * * *